(12) United States Patent
Tingey

(10) Patent No.: US 7,890,193 B2
(45) Date of Patent: Feb. 15, 2011

(54) ORAL DEVICE

(76) Inventor: Terrell F. Tingey, 2020 N. Cole Rd., Boise, ID (US) 83704

( * ) Notice: Subject to any disclaimer, the term of this patent is extended or adjusted under 35 U.S.C. 154(b) by 756 days.

(21) Appl. No.: 11/839,362

(22) Filed: Aug. 15, 2007

(65) Prior Publication Data

US 2009/0048647 A1   Feb. 19, 2009

(51) Int. Cl.
*A61N 1/00* (2006.01)
(52) U.S. Cl. ..................................... 607/134
(58) Field of Classification Search ........................ None
See application file for complete search history.

(56) References Cited

U.S. PATENT DOCUMENTS

| | | |
|---|---|---|
| 3,983,865 A | 10/1976 | Shepard |
| 4,220,142 A | 9/1980 | Rosen et al. |
| 4,669,477 A | 6/1987 | Ober |
| 4,715,367 A | 12/1987 | Crossley |
| 4,934,378 A | 6/1990 | Perry, Jr. |
| 4,976,618 A | 12/1990 | Anderson |
| 4,995,404 A | 2/1991 | Nemir |
| 5,078,153 A | 1/1992 | Nordlander et al. |
| 5,143,087 A | 9/1992 | Yarkony |
| 5,212,476 A * | 5/1993 | Maloney ............... 340/825.19 |
| 5,553,626 A | 9/1996 | Burger et al. |
| 5,586,562 A | 12/1996 | Matz |
| 5,989,023 A * | 11/1999 | Summer et al. ............... 433/69 |
| 6,089,864 A | 7/2000 | Buckner et al. |
| 6,093,158 A | 7/2000 | Morris |
| 6,117,092 A | 9/2000 | Weinstein et al. |
| 6,231,500 B1 | 5/2001 | Kehoe |
| 6,270,466 B1 | 8/2001 | Weinstein et al. |
| 6,511,441 B1 * | 1/2003 | Wakumoto et al. .......... 600/590 |
| 6,544,199 B1 | 4/2003 | Morris |
| 6,597,944 B1 | 7/2003 | Hadas |
| 6,613,001 B1 | 9/2003 | Dworkin |
| 6,638,241 B2 | 10/2003 | Yerushalmy |
| 7,059,332 B2 | 6/2006 | Eli |
| 2005/0222503 A1 | 10/2005 | Dunlop et al. |
| 2006/0060208 A1 | 3/2006 | Eli |
| 2007/0173893 A1 * | 7/2007 | Pitts ............................... 607/2 |

* cited by examiner

*Primary Examiner*—Mark W Bockelman
*Assistant Examiner*—Elizabeth K So
(74) *Attorney, Agent, or Firm*—Robert L. Shaver

(57) ABSTRACT

The invention is a removable plastic oral appliance which includes sensors for detecting the position of a patient's tongue and mandible. Pressure sensors in the appliance itself detect tongue contact and pressure against the palate or the lower teeth against the upper teeth. The sensors are connected electronically to an electronic processor which interprets the information against one or more contra-indicated tongue or jaw positions or activities, and selects an appropriate response from a pre-selected range of responses. The electronic processor sends a signal to a stimulus electrode to cause the patient to stop the contraindicated tongue position, jaw position, or activity.

15 Claims, 1 Drawing Sheet

ORAL DEVICE

FIELD OF THE INVENTION

The present invention generally relates to an oral rehabilitation device, and more particularly to an oral device for training a patient in tongue and jaw position.

BACKGROUND OF THE INVENTION

Dysfunction of the oral muscles presents itself in many forms and occurs with alarming frequency in the population. Most harmful oral habits occur on a subconscious level or during sleep. Treating incorrect behavior of the muscles of the tongue and the muscles of mastication are of interest to dentists, physicians, and speech therapists.

Tongue function. The proper rest posture for the tongue is flat against the palate (roof of the mouth). In the growing child, the lateral growth of the maxilla is stunted when the tongue does not rest in the palate. Cross bites, crowding and poor occlusion are commonly seen. During sleep, the tongue should maintain posture subconsciously against the palate. If the tongue fails to maintain contact against the palate, it can fall back to a position in the pharynx that obstructs respiration. This is one of the causes of snoring and sleep apnea. A person with significant structural or inflammatory nasal obstruction is obliged to breathe through the mouth. In this case, the tongue rests inferiorly on the floor of the mouth to allow the passage of air through the lips, over the tongue, and into the pharynx. Proper tongue rest position cannot be established with out medical relief of the nasal obstruction. Removal of the obstruction does not always change the tongue posture. Inferior tongue posture in these individuals seems to be habitual, or a behavioral error.

The swallow is a reflexive behavior, but can be consciously controlled. The correct swallowing motion for the tongue is performed with the lower posterior teeth touching the upper posterior teeth and the tongue remaining against the roof of the mouth. The pressure at the tip of the tongue is increased against the anterior palate and the contact area rolls posteriorly sweeping the bolus of food or liquid into the pharynx. A common error in swallowing occurs in persons who thrust their tongue anteriorly between the upper and lower front teeth. This is sometimes called a "tongue thrust" or "infantile swallow." The repetitive forceful contact of the tongue against the incisal edges of the upper and lower anterior teeth produces an intrusive force against the incisors. The tongue thruster also fails to bring the lower posterior teeth against the upper posterior teeth, which results in excessive vertical growth of the posterior teeth. The result is an open bite malocclusion with no contact or vertical overlap of the upper and lower incisors. In some instances the tongue will thrust laterally instead of anteriorly, causing a lack of occlusal contact in one or both sides of the dentition. Successful treatment requires training correct swallowing behavior.

Proper speech requires the adept coordination of movement of the vocal chords, lips and tongue, with feedback from hearing. Many individuals have difficulty with correct tongue position and exhibit poor control and strength of the tongue. Therapeutic exercises are usually prescribed to correct the articulation errors.

Masticatory muscle loading. The muscles of mastication are normally active during chewing, and briefly during swallowing. Muscle contraction outside of these activities is considered to be dysfunctional. It is termed bruxism, clenching or grinding. This behavior is believed to be a response to stress, pain, and irregular occlusion. It causes pain, joint damage, dental attrition, and periodontal damage. Long-term bruxism also causes hypertrophy of the masticatory muscles and may, through intrusion of the posterior teeth, structurally reduce lower facial height. Most treatments of bruxism are designed to reduce the intensity of the muscle loading or shield the oral structures from the effects of non-physiologic forces.

Conversely, hypoactive masticatory muscles, that fail to load during swallowing, contribute to the creation of open bite malocclusion. In such individuals, the erupting lower and upper teeth often fail to meet in a balanced cusp-fossa relationship. The contacts between the upper and lower teeth will usually be few, and located mostly in the posterior regions. With time, the posterior teeth will be worn flat, requiring repair. The unchecked passive eruption of the posterior teeth causes increased lower facial height, and a dolicocephalic facial form. Current treatments may surgically improve the skeletal dimensions in such cases, but no treatment has yet been shown to strengthen and tone the masticatory muscles.

SUMMARY

These and other objectives are accomplished by the oral appliance of the invention. The oral appliance of the invention is for training a patient in the posture and function of the tongue. The device includes an appliance body, which is configured for placement in a patient's mouth, adjacent the patient's tongue and teeth. The appliance body includes one or more tongue parameter sensors mounted in the appliance body for detecting certain parameters related to a patient's tongue. These can include tongue position, tongue pressure, the tongue contact duration, the interval between contact of a patient's tongue against the appliance body.

The oral appliance includes an electronic processor for receiving a signal from the tongue parameter sensors. The electronic processor may be mounted in the appliance body, and it may also be positioned at a distance from the appliance body, such as outside the patient's mouth, and either tethered to the appliance body or connected wirelessly to the appliance body. The electronic processor is configured to receive a signal from the tongue parameter sensors and to select a response to the sensors based on a predetermined selection of appropriate responses. The appliance body includes one or more stimulus electrodes for contact with a part of the patient. The stimulus electrodes are provided for delivering a feedback stimulus to the patient. The stimulus electrodes would be positioned to contact the oral mucosa of a patient, or could also be configured to contact the patient's skin in some location outside the patient's mouth. The stimulus electrodes can be part of the appliance body, or could also be positioned at a distance from the appliance body. For instance, a stimulus electrode could be placed on a patient's ear lobe, fingertip or other convenient location, and could be connected to the appliance body by a wire or by a wireless electronic connection. The device also includes one or more stimulus generators for generating a feedback stimulus and delivering the feedback stimulus to the stimulus electrodes. The stimulus would be based on information from the electronic processor, based on the patient's tongue parameters. A power source is also provided for providing energy to the stimulus generator.

One tongue parameter which may be sensed is tongue position. Tongue position is sensed by one or more tongue position sensors, which relay information about tongue position to the electronic processor. A programmable microprocessor is provided in the device for recording tongue parameters over time from the tongue parameter sensors, which may include tongue position sensors. The electronic processor forms a response to the tongue parameters in the form of a feedback stimulus delivered to the patient.

Another tongue parameter which may be sensed is tongue pressure. Tongue pressure is sensed by the use of one or more tongue pressure sensors.

The feedback stimulus provided to the patient can be in the form of an electric shock, which is generally directed to the patient via one or more stimuli. The appliance body is typically attached to the patient's upper teeth and/or upper palate.

The device may also include one or more sensors for jaw position, which send a signal related to jaw position to an electronic processor. The electronic processor would select a response based on the detected tongue parameters and jaw position and deliver that response to the stimulus electrodes. The jaw position sensed is whether the jaw is open or closed.

One version of the device includes sensors for both tongue position and jaw position.

DESCRIPTION OF THE PREFERRED EMBODIMENTS

Figure 1:
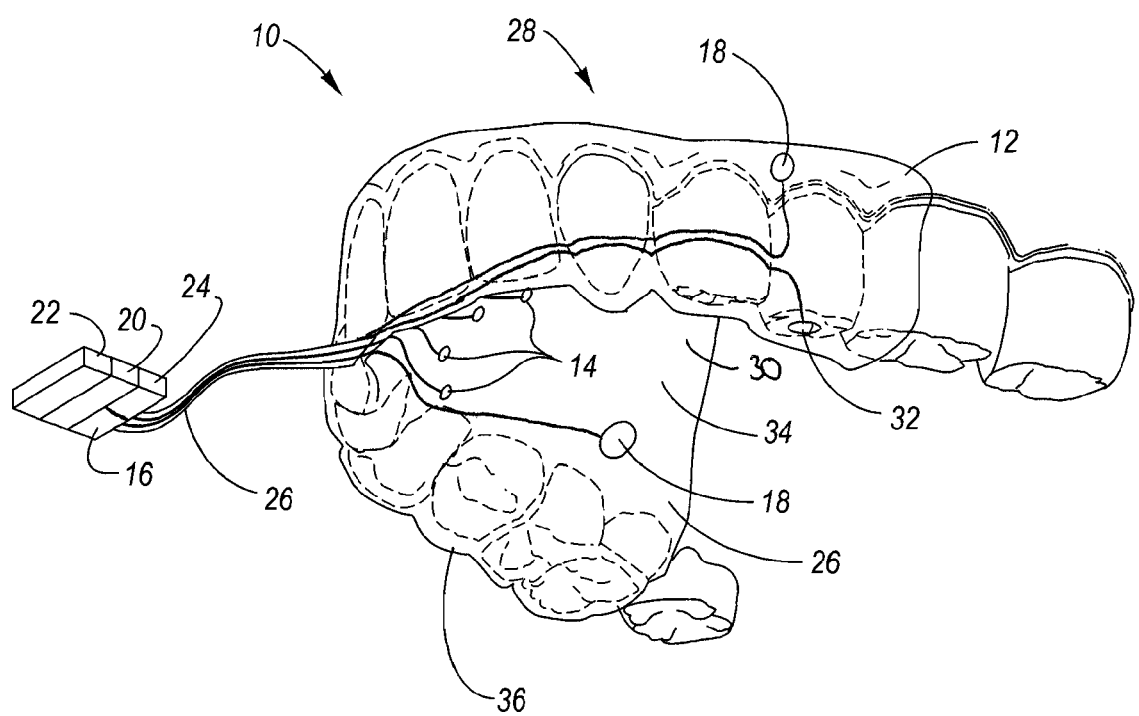
FIG. 1 is a perspective view of the oral appliance of the invention.

While the invention is susceptible of various modifications and alternative constructions, certain illustrated embodiments thereof have been shown in the drawings and will be described below in detail. It should be understood, however, that there is no intention to limit the invention to the specific form disclosed, but, on the contrary, the invention is to cover all modifications, alternative constructions, and equivalents falling within the spirit and scope of the invention as defined in the claims.

In the following description and in the FIGURE, like elements are identified with like reference numerals. The use of "or" indicates a non-exclusive alternative without limitation unless otherwise noted. The use of "including" means "including, but not limited to," unless otherwise noted.

FIG. 1 shows a preferred embodiment of the oral appliance of the invention, referred to as 10, which includes an appliance body 12. The appliance body 12 may be generally configured like a prior art orthodontic retainer, and can be made of hard or soft plastic or other suitable materials. Embedded in the appliance body 12 are one or more tongue parameter sensors 14. Tongue parameter sensors 14 are configured to measure one or all of several tongue parameters, including force, pressure, and touch. To detect the position of the tongue, parameter sensors 14 are primarily configured to detect touch or a light force or light pressure. The appliance body can be formed from a dental impression and cast, or may be made in a range of different sizes for different size mouths. It may also be provided to a patient in a form that enables him to fit the device to his teeth in a forming step, such as with heat formable material.

Technology which is suitable for the tongue parameter sensors 14 includes strain gauges, piezoresistors, air pressure sensors, and capacitance touch switches. These and other standard and readily available electronic technologies can serve as a basis for the tongue parameters sensors 14. Electrical connections between the tongue parameter sensors 14 and the electronic processor 16 are provided by conductive pathways which may be copper wires embedded in the matrix of the appliance body 12, or which can also be painted or etched or otherwise affixed to the outside surfaces of the appliance body 12. For instance, a conductive paint can form a link between the tongue parameter sensors 14 and the electronic processor 16. Also, conductive pathways can be applied using an adhesive to either surface of the appliance body 12.

The electronic processor 16 receives signals from the tongue parameter sensors 14, interprets them and responds with a response appropriate to the condition being treated. If a response was needed it would typically be an electronic stimulus produced by a stimulus generator 20, and would require energy from a power source 22. The electronic processor 16 would send a signal to one or more stimulus electrodes 18, positioned on the ventral side 30 of the appliance body 12. In this particular configuration the electronic components are connected by a tether 26, and the electronic processor 16, stimulus generator 20, and power source 22 are located exterior to the patient's mouth. The power source could be in the form of a battery for instance. These components could also be made in a wireless mode, and in the wireless mode these components could be located anywhere near the patient and the appliance body 12. For instance, these components would be attached to the patient's pillow or clothing, worn on a wrist strap, or attached to the patient's bed or any other furniture. In miniature format, the electronics components could also be located on the appliance body 12. Feedback can also be in the form of a visual cue, or an audible cue, or as a vibration or other tactile cue.

Parameters that the tongue parameter sensors 14 would be configured to detect would include the time of contact, or the lack of contact of the tongue to the palate, or the lack of contact of the tongue from one tooth to another. In response to information such as this, a stimulus generator 20 would send the pre-selected stimulus to electrodes 18. Examples of tongue position detection would include the normal tongue-up and forward position, and abnormal tongue-down position, or tongue-back position, and abnormal tongue-forward position. Other conditions the device could be used with include tongue thrust swallow, mouth breathing, low tongue posture, posterior pharyngeal constriction, speech impediment, clenching and bruxism.

The electronic processor 16, or a version of the processor which is programmable, is shown in FIG. 3 as programmable processor 24, would be configured to interpret data to evaluate such patient activities as "tongue up" posture, "tongue back" posture, too much clenching of the jaw, too little clenching of the jaw, etc. Other abnormal jaw position conditions which would be sensed include the normal teeth apart position, and abnormal teeth together positions, and the normal swallow teeth-together position. The tongue parameter 14 sensors would be located in different positions and the type of sensors would be modified for the specific problem for which the patient was being treated. A different electronic processor 16 or appliance body 12 might be supplied for each of the different kinds of tongue and jaw related problems that the device could handle. It is also possible that one appliance body 12 and one electronic processor 16 or programmable processor 24 could be utilized to detect and treat some or all of these tongue and jaw position situations.

The tongue parameter sensors 14 are located on the oral side 30, and the stimulus electrodes are on the tissue side 28. Included in FIG. 1 is a palate portion 34. Although the preferred embodiment, the palate portion 34 is optional. In addition to the palate portion 34, the device includes a semicircular tooth area portion 36 of the appliance body 12. This portion of the appliance body of this embodiment is basically equivalent to a soft mouth guard and would typically be fit to a person's teeth so that a comfortable fit is achieved. A jaw position sensor 32 may be present. The jaw position sensor 32 senses when the patient's jaw is in a closed or open position, by sensing contact with a tooth in the lower jaw adjacent to the jaw position sensor. The programmable processor 24 has pre-selected interpretation instructions for interpreting the signals from the tongue parameter sensors 14 and the jaw position sensors 32. Based on information received from each of these types of sensors, and the condition being treated, the programmable processor 24 would send a stimulus to the stimulus electrodes 18.

The stimulus sent to the stimulus electrodes 18 would typically be a very light electric shock, which would typically but not necessarily be calibrated to be insufficient to wake a patient up. However it would at least raise the patent's level of consciousness to a level to cause correction of the contraindicated behavior related to jaw or tongue position. In this manner a bio feedback loop would be established to train the patient to not perform the contraindicated behaviors, including certain tongue positions and jaw positions. This conditioning would follow the strategy of classical conditioning and over a period of time would teach the patient to develop new habits of tongue posture and jaw position.

Components include:

1. A removable plastic retainer-like oral appliance, custom made from an upper or lower dental cast of the patient's teeth.
2. One or more electronic pressure sensors located on the palate, lower lingual, and occlusal surfaces of the plastic appliance. The sensor may be a strain gage, load cell, contact switch or other piezoelectric sensor. The sensors connect to extra-oral electronics through electric wires exiting the mouth between the lips, or wireless radio frequency transmission.
3. Stimulus electrodes are embedded in the appliance, contacting the oral mucosa and the palate.
4. Electronic circuitry in a compact box is tethered to the retainer and worn on the head or torso. A version in which the electronics circuitry is entirely contained in the retainer is envisioned.
5. Sensor powering and detection circuit.
6. Programmable microprocessor records forces of the tongue against the palate and teeth, or lower teeth against the upper teeth. The processor evaluates sensor data. Data is evaluated for contact force, contact duration, and the interval between contacts. If the sensor detects undesirable tongue and tooth contacts, it activates the "prod" circuit.
7. Stimulus generator delivers a non painful, but annoying electric shock (prod) to the palate.

Variations of the Electric biofeedback oral trainer include:

1. EBOT-tp (electric biofeedback oral trainer-tongue in palate) the sensor is in the anterior palate to train the tongue to rest against the anterior palate. Treatment for tongue thrust, snoring and sleep apnea.
2. EBOT-b (electric biofeedback oral trainer-bruxer) the sensor is on the occlusal surface of the teeth to train the lower jaw to adopt a rest position with the teeth slightly apart. Treatment for bruxism, temporomandibular symptoms.
3. EBOT-ob (electric biofeedback oral trainer-open bite) the sensor is on the occlusal surface of the posterior teeth to increase the frequency, duration, and magnitude of clenching behavior.
4. EBOT-s (electric biofeedback oral trainer-speech) the sensors are located on the palate to encourage site-specific contact from the tongue against the palate. Treatment for correction of speech articulation errors, and conditions the tongue for improved strength and coordination.

While there is shown and described the present preferred embodiment of the invention, it is to be distinctly understood that this invention is not limited thereto, but may be variously embodied to practice within the scope of the following claims. From the foregoing description, it will be apparent that various changes may be made without departing from the spirit and scope of the invention as defined by the following claims.

I claim:

1. An oral appliance for training of a patient for proper posture and function of the tongue comprising:
   an appliance body with an oral side and a tissue side, configured for engagement with a patient's upper teeth and anterior palate;
   one or more tongue parameter sensors mounted on said oral side of said appliance body, for detecting parameters of a patient's tongue relating to palate contact by said tongue;
   an electronic processor for receiving a signal from said tongue parameter sensors related to tongue position against said palate, and for selecting a response based on the detected tongue palate contact information;
   one or more stimulus electrodes on said tissue side of said appliance body for contact with an upper mucosa region on said palate of said patient, for delivering a feedback stimulus to said palate to alert said patient in response to a detected tongue palate parameter;
   one or more stimulus generators, for creating said feedback stimulus and sending said stimulus to said stimulus electrodes, based on information from said electronic processor; and
   a power source for providing energy to said one or more stimulus generators.

2. The oral appliance of claim 1 in which the tongue parameter sensed is tongue position, and which further comprises one or more tongue position sensors, for sensing a position of said patient's tongue in relation to said patient's palate.

3. The oral appliance of claim 2 which further comprises a programmable microprocessor for recording tongue parameters over time from said tongue position sensors, with said electronic processor forming a response to said tongue parameters in the form of a feedback stimulus delivered to said palate of said patient.

4. The oral appliance of claim 1 which further comprises a programmable microprocessor for recording tongue parameters over time from said tongue position parameter sensors, with said electronic processor forming a response to said tongue parameters in the form of a feedback stimulus delivered to the palate of said patient.

5. The oral appliance of claim 1 in which the tongue parameter sensed is tongue pressure, and which further comprises one or more tongue pressure sensors, for sensing pressure of said patient's tongue against the patient's teeth and/or palate.

6. The oral appliance of claim 1 in which a tongue parameter sensed is contact force of the patient's tongue against the appliance body.

7. The oral appliance of claim 1 in which a tongue parameter sensed is contact duration of the patient's tongue against the appliance body.

8. The oral appliance of claim 1 in which a parameter sensed is the time interval between contacts of the patient's tongue against the appliance body.

9. The oral appliance of claim 1 in which said feedback stimulus is an electric shock.

10. The oral appliance of claim 1 which includes a tether for connecting internal components of the appliance inside the patient's mouth to external components outside the patient's mouth.

11. The oral appliance of claim 1 in which said appliance body is fitted to the patient's upper teeth.

12. The oral appliance of claim 1 in which said appliance body is positioned near the incisal edge of the upper and lower teeth for training the patient in protrusive tongue thrust behavior.

13. The oral appliance of claim 1 which further includes one on more sensors for jaw position, which send a signal related to jaw position to an electronic processor, with said electronic processor for selecting a response based on the detected tongue parameters and jaw position.

14. An oral appliance for training a patient in proper posture and function of the tongue, comprising:
- an appliance body configured for engagement with a patient's anterior palate, with an oral side and a tissue side;
- one or more tongue position sensors mounted on said oral side of said appliance body for detecting the presence of a patient's tongue against said appliance body;
- an electronic processor for receiving a signal from the position sensors related to tongue position against said palate, and for selecting a response based on the detected tongue position;
- one or more stimulus electrodes on the tissue side of said appliance body for contact with an upper mucosa region on said palate for delivering a feedback stimulus to said palate to alert said patient, in the form of an electric shock to the patient in response to feedback from said one or more tongue position sensors;
- one or more stimulus generators, for creating said feedback stimulus and sending said stimulus to said stimulus electrodes, based on information from said electronic processor;
- a power source for providing energy to said stimulus generators; and
- a programmable microprocessor for recording parameters of tongue contact against said appliance body over time, for parameters of tongue position, tongue contact duration, and interval between contact of a patient's tongue against the appliance body, with said tongue position sensors for prompting a response to said tongue parameters in the form of a feedback stimulus.

15. An oral appliance for training a patient in proper posture and function of the tongue and jaw position, comprising:
- an appliance body configured for placement in a patient's mouth, adjacent the patient's anterior palate;
- one or more tongue position sensors for detecting the position of a patient's tongue and for generating tongue parameters;
- one or more jaw position sensors for detecting the position of a patient's mandible and for generating jaw position parameters;
- an electronic processor for receiving a signal from the sensors related to tongue position and jaw position, and for selecting a response based on the detected tongue and jaw position;
- one or more stimulus electrodes for delivering a feedback stimulus to the upper mucosa in the form of an electric shock to the patient in response to feedback from said one or more tongue position sensors;
- one or more stimulus generators, for creating said feedback stimulus and sending said stimulus to said stimulus electrodes, based on information from said electronic processor;
- a power source for providing energy to said stimulus generator; and
- a programmable microprocessor for recording parameters of tongue and mandible position over time, including tongue contact force, tongue contact duration, and interval between contact of a patient's tongue against the appliance body, with said tongue position sensor forming a response to said tongue and jaw position parameters in the form of a feedback stimulus.

* * * * *